United States Patent
Masumoto et al.

(10) Patent No.: US 8,903,039 B2
(45) Date of Patent: Dec. 2, 2014

(54) TOMOGRAPHIC IMAGE GENERATION DEVICE AND METHOD

(71) Applicant: FUJIFILM Corporation, Tokyo (JP)

(72) Inventors: Jun Masumoto, Ashigarakami-gun (JP); Masahiko Yamada, Ashigarakami-gun (JP); Hiroaki Yasuda, Ashigarakami-gun (JP); Yasuko Yahiro, Ashigarakami-gun (JP); Nobuhiko Kashiwagi, Ashigarakami-gun (JP); Ayako Muramoto, Ashigarakami-gun (JP); Haruyasu Nakatsugawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/019,315

(22) Filed: Sep. 5, 2013

(65) Prior Publication Data
US 2014/0093036 A1  Apr. 3, 2014

(30) Foreign Application Priority Data

Sep. 28, 2012 (JP) .................................. 2012-215848

(51) Int. Cl.
H05G 1/60 (2006.01)
G06K 9/36 (2006.01)
G06K 9/60 (2006.01)
A61B 6/02 (2006.01)
A61B 6/00 (2006.01)

(52) U.S. Cl.
CPC ................. *A61B 6/502* (2013.01); *A61B 6/025* (2013.01); *A61B 6/5205* (2013.01); *Y10S 378/901* (2013.01)

USPC .............. 378/21; 378/901; 382/131; 382/233

(58) Field of Classification Search
USPC ........ 378/21–27, 37, 91, 98, 98.12, 204, 210, 378/901; 382/128, 131, 166, 232–234, 244, 382/325
See application file for complete search history.

(56) References Cited

U.S. PATENT DOCUMENTS

| 5,471,987 | A  | * | 12/1995 | Nakazawa et al. ............ 600/436 |
| 5,991,457 | A  | * | 11/1999 | Ito et al. ........................ 382/254 |
| 6,115,486 | A  | * | 9/2000  | Cantoni ........................ 382/128 |
| 2007/0065032 | A1 | * | 3/2007 | Hernandez et al. ........... 382/239 |
| 2007/0065033 | A1 | * | 3/2007 | Hernandez et al. ........... 382/239 |
| 2008/0187095 | A1 |   | 8/2008 | Boone et al. |
| 2008/0247509 | A1 |   | 10/2008 | Kashiwagi |

OTHER PUBLICATIONS

Chinese Office Action dated Jul. 25, 2014 with a partial English translation thereof.

* cited by examiner

*Primary Examiner* — Anastasia Midkiff
(74) *Attorney, Agent, or Firm* — McGinn IP Law Group, PLLC

(57) ABSTRACT

Radiographic images for different imaging directions taken by applying radiation to a subject from the different imaging directions are obtained, and a plurality of tomographic images of the subject are generated based on the obtained plurality of radiographic images. Then, compression processing in the direction perpendicular to slice planes of the generated tomographic images is applied to the tomographic images to generate compressed tomographic images, wherein a range of the imaging directions is obtained, and a compression rate of the compression processing is set based on the obtained range of the imaging directions.

14 Claims, 8 Drawing Sheets

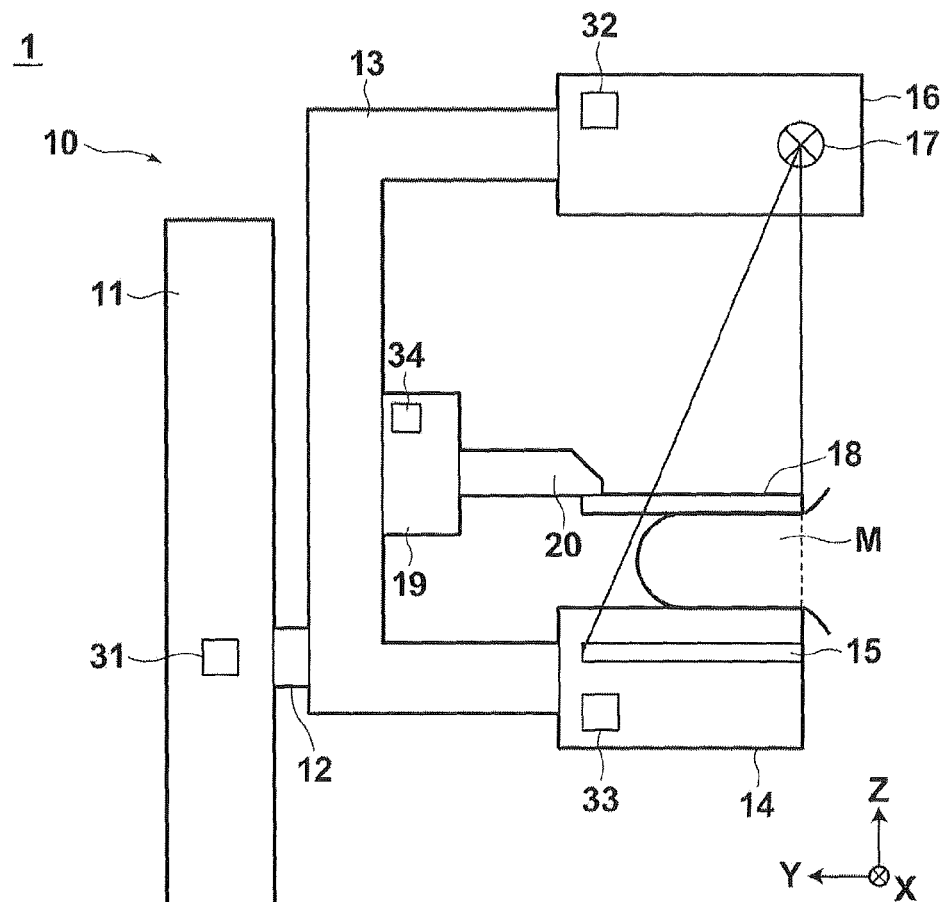
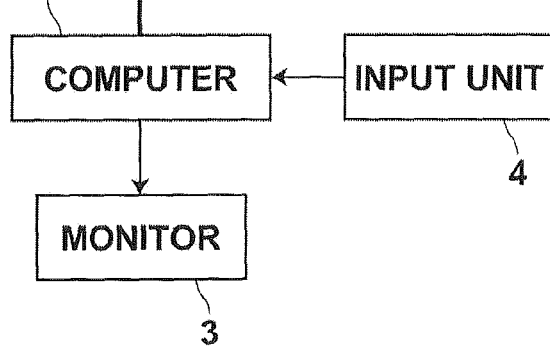
FIG.1

TOMOGRAPHIC IMAGE GENERATION DEVICE AND METHOD

BACKGROUND OF THE INVENTION

1. Field of the Invention

The present invention relates to a tomographic image generation device and a tomographic image generation method wherein a plurality of tomographic images of a subject are generated based on a plurality of radiographic images obtained by applying radiation to the subject from different imaging directions, and compression processing is applied to the generated tomographic images.

2. Description of the Related Art

In recent years, in order to observe an affected part of the body in more detail using a radiographic imaging apparatus, tomosynthesis imaging is proposed, where imaging operations are performed with applying radiation to the subject from different imaging directions by moving the radiation source to obtain a plurality of radiographic images, and the radiographic images are added to provide an image in which a desired slice plane is emphasized (see, for example, U.S. Patent Application Publication No. 20080247509).

In the tomosynthesis imaging, radiographic images of the subject, which are taken at different exposure angles with moving the radiation source parallel to the radiographic image detector or along a circular or elliptical trajectory depending on the characteristics of the imaging apparatus and necessary tomographic images, are obtained, and the radiographic images are reconstructed to generate tomographic images. Specifically, the tomographic images can be obtained by adding the radiographic images after shifting the radiographic images relative to one another, adjusting the size of each radiographic image, etc.

Further, it is proposed to develop the above-described tomosynthesis imaging to the mammography.

SUMMARY OF THE INVENTION

However, since the tomosynthesis imaging generates the tomographic images by adding the radiographic images after shifting, etc., of the radiographic images, which are taken from different imaging directions, as described above, information in the direction perpendicular to the slice planes of the tomographic images is scant. Therefore, when volume rendering is performed using these tomographic images, each tomographic image is influenced by information of the tomographic images adjacent to the tomographic image in the direction perpendicular to the slice plane, and it is difficult to observe a three-dimensional structure intended to be observed.

Further, in the mammography, imaging operations are performed in a state where the breast is compressed, and therefore the interval in the direction perpendicular to the slice planes does not have much meaning.

Still further, while the mammographic imaging is performed in the state where the breast is compressed, as described above, when a three-dimensional image is reconstructed based on the radiographic images obtained by the imaging, an isotropic reconstructed image is generated. Therefore, the dimension size in the Z-direction (the direction perpendicular to the slice planes) is greater than those in the X-direction and the Y-direction, resulting in a three-dimensional image with the size of a structure in the Z-direction being extended from the actual size of the structure.

In view of the above-described circumstances, the present invention is directed to providing a tomographic image generation device and a tomographic image generation method where the size of a structure in a three-dimensional image generated by reconstructing tomographic images is made close to the actual size of the structure, thereby facilitating understanding of the three-dimensional structure and improving the diagnosis accuracy.

An aspect of the tomographic image generation device of the invention is a tomographic image generation device for generating tomographic images based on radiographic images for different imaging directions taken by applying radiation to a subject from the different imaging directions, the device including: a radiographic image obtaining unit for obtaining the radiographic images for the different imaging directions; a tomographic image generation unit for generating a plurality of tomographic images of the subject based on the plurality of radiographic images obtained by the radiographic image obtaining unit; a compression processing unit for applying compression processing in a direction perpendicular to slice planes of the tomographic images to the tomographic images generated by the tomographic image generation unit to generate compressed tomographic images; an imaging direction range obtaining unit for obtaining a range of the imaging directions; and a compression rate setting unit for setting a compression rate of the compression processing based on the range of the imaging directions obtained by the imaging direction range obtaining unit.

The tomographic image generation device of the invention may further include a number of images determining unit for obtaining a total number of the compressed tomographic images to be generated based on the compression rate set by the compression rate setting unit and determining whether or not the total number is not greater than a threshold value, wherein, if it is determined by the number of images determining unit that the total number of the compressed tomographic images is greater than the threshold value, the imaging direction range obtaining unit obtain a new value of the range of the imaging directions, and the compression rate setting unit set a new compression rate of the compression processing based on the obtained new value of the range of the imaging directions.

The tomographic image generation device of the invention may further include a compression rate change receiving unit for receiving a change to the compression rate, wherein the compression rate setting unit sets a new compression rate of the compression processing based on a changed compression rate received by the compression rate change receiving unit.

The tomographic image generation device of the invention may further include a three-dimensional image generation unit for generating a three-dimensional image of the subject based on the compressed tomographic images generated by the compression processing unit.

The tomographic image generation device of the invention may further include a display control unit for displaying a superimposition image of the three-dimensional image superimposed on the radiographic image, the tomographic image or the compressed tomographic image.

The tomographic image generation device of the invention may further include an area specifying unit for receiving a specification of a desired area on the radiographic image, the tomographic image or the compressed tomographic image, wherein the display control unit displays a superimposition image of the three-dimensional image superimposed on the radiographic image, the tomographic image or the compressed tomographic image, the three-dimensional image containing the area received by the area specifying unit.

The display control unit may display the three-dimensional image and the radiographic image, the tomographic image or the compressed tomographic image of the superimposition image in different colors from each other.

The display control unit may display the radiographic image, the tomographic image or the compressed tomographic image side by side with the superimposition image.

The display control unit may display the superimposition image in a rotated state.

The display control unit may display markers at a position on the subject on the radiographic image, the tomographic image or the compressed tomographic image and a position on the superimposition image corresponding to the position on the subject.

The tomographic image generation device of the invention may further include an image selection receiving unit for receiving a selection of any one of the radiographic images, the tomographic images or the compressed tomographic images to be displayed.

The tomographic image generation device of the invention may further include a color change receiving unit for receiving a change to the color of the three-dimensional image.

The tomographic image generation device of the invention may further include a display range receiving unit for receiving a display range or position of the three-dimensional image.

An aspect of the tomographic image generation method of the invention is a tomographic image generation method for generating tomographic images based on radiographic images for different imaging directions taken by applying radiation to a subject from the different imaging directions, the method including: obtaining the radiographic images for the different imaging directions; generating a plurality of tomographic images of the subject based on the obtained plurality of radiographic images; and applying compression processing in a direction perpendicular to slice planes of the generated tomographic images to the tomographic images to generate compressed tomographic images, wherein a range of the imaging directions is obtained, and a compression rate of the compression processing is set based on the obtained range of the imaging directions.

According to the tomographic image generation device and method of the invention, radiographic images for different imaging directions taken by applying radiation to a subject from the different imaging directions are obtained, and a plurality of tomographic images of the subject are generated based on the obtained plurality of radiographic images. Then, compression processing in the direction perpendicular to slice planes of the generated tomographic images is applied to the tomographic images to generate compressed tomographic images. Then, by reconstructing a three-dimensional image using the compressed tomographic images, the dimension size in the Z-direction (the direction perpendicular to the slice planes) can be made close to the dimension sizes in the X-direction and Y-direction. This allows making the size of a structure in the three-dimensional image close to the actual size of the structure, thereby facilitating understanding of the three-dimensional structure and improving the diagnosis accuracy.

Further, according to the invention, a range of the imaging directions of the radiographic images used to generate the tomographic images is obtained, and a compression rate of the compression processing is set based on the obtained range of the imaging directions. Therefore, the compression processing can be performed without degrading the image quality of the compressed tomographic images. The reason of setting the compression rate based on the range of the imaging directions of the radiographic images will be described in detail later.

Further, in a case where the tomographic image generation device and method of the invention is configured such that the total number of the compressed tomographic images to be generated by the compression processing is obtained based on the compression rate that is set depending on the range of the imaging directions, whether or not the total number is not greater than a threshold value is determined, and if it is determined that the total number of the compressed tomographic images is greater than the threshold value, then a new value of the range of the imaging directions is obtained, and a new compression rate of the compression processing is set based on the obtained range of the imaging directions, the total number of the compressed tomographic images can be limited, thereby reducing the time taken for image interpretation of the compressed tomographic images.

BRIEF DESCRIPTION OF THE DRAWINGS

FIG. 1 is a diagram illustrating the schematic structure of a mammographic imaging and display system employing one embodiment of a tomographic image generation device of the present invention.

DESCRIPTION OF THE PREFERRED EMBODIMENTS

Figure 2:
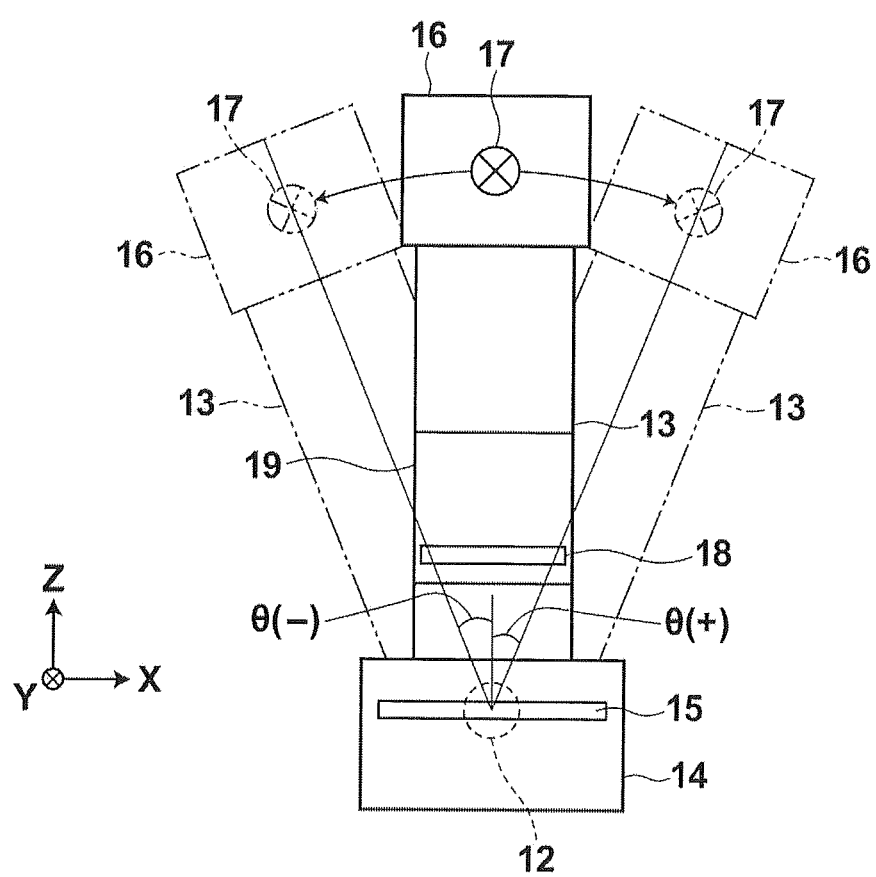
FIG. 2 is a diagram illustrating an arm of the mammographic imaging and display system shown in FIG. 1 viewed from the right side in FIG. 1.

Now, a mammographic imaging and display system employing a first embodiment of a tomographic image generation device and a tomographic image generation method of the present invention will be described with reference to the drawings. The mammographic imaging and display system of this embodiment has a tomosynthesis imaging function, and is configured to be capable of taking tomographic images of the breast. FIG. 1 is a diagram illustrating the schematic configuration of the entire mammographic imaging and display system of this embodiment.

As shown in FIG. 1, a mammographic imaging and display system 1 of this embodiment includes: a mammographic imaging apparatus 10 for obtaining radiographic images of a breast, which is the subject, for different imaging directions by applying radiation to the breast from the different imaging directions; a computer 2 for reconstructing the plurality of radiographic images obtained by the mammographic imaging apparatus 10 to generate a plurality of tomographic images of the breast and generating a three-dimensional image of the breast based on the tomographic images; a monitor 3 for displaying the tomographic image, the three-dimensional image, or the like, generated by the computer 2; and an input unit 4 for receiving various settings inputted by the user.

As shown in FIG. 1, the mammographic imaging apparatus 10 includes a base 11, a rotation shaft 12 that is rotatable and is movable in the vertical direction (Z-direction) relative to the base 11, and an arm 13 that is connected to the base 11 via the rotation shaft 12. FIG. 2 shows the arm 13 viewed from the right side of FIG. 1.

The arm 13 is C-shaped, and is provided with an imaging table 14 at one end thereof and a radiation exposure unit 16 at the other end thereof such that the radiation exposure unit 16 faces the imaging table 14. The rotation and the movement in the vertical direction of the arm 13 are controlled by an arm controller 31, which is built in the base 11.

The imaging table 14 contains therein a radiographic image detector 15, such as a flat panel detector, and a detector controller 33, which controls reading of electric charge signals from the radiographic image detector 15, etc.

The imaging table 14 also contains therein a circuit board, etc. The circuit board includes a charge amplifier for converting the electric charge signals read out from the radiographic image detector 15 into voltage signals, a correlated double sampling circuit for sampling the voltage signals outputted from the charge amplifier, an AD converter for converting the voltage signals into digital signals, etc.

As shown in FIG. 2, the imaging table 14 is attached to the arm 13 in such a positional relationship that the center of the radiographic image detector 15 is located on an extended line of the rotating shaft 12. The imaging table 14 is rotatably attached to the arm 13, and the orientation of the imaging table 14 can be fixed relative to the base 11 even when the arm 13 is rotated relative to the base 11.

The radiographic image detector 15 is of a type that is repeatedly usable to record and read a radiographic image. The radiation detector 15 may be a so-called direct-type radiographic image detector, which directly receives the radiation and generates electric charges, or may be a so-called indirect-type radiographic image detector, which once converts the radiation into visible light, and then converts the visible light into electric charge signals. As the reading system to read out the radiographic image signal, a so-called TFT reading system, which reads out the radiographic image signal with turning on and off TFT (thin film transistor) switches, or a so-called optical reading system, which reads out the radiographic image signal by applying reading light, may be used. As the indirect-type radiographic image detector, one using a CMOS (Complementary Metal Oxide Semiconductor) sensor or a CCD (Charge Coupled Device Image Sensor) may be used.

The radiation exposure unit 16 contains therein a radiation source 17 and a radiation source controller 32. The radiation source controller 32 controls timing of application of radiation from the radiation source 17, and radiation generation conditions (such as tube current, time, tube voltage, etc.) at the radiation source 17.

Further, a compression paddle 18 disposed above the imaging table 14 for holding and compressing the breast, a support 20 for supporting the compression paddle 18, and a moving mechanism 19 for moving the support 20 in the vertical direction (Z-direction) are disposed at the middle portion of the arm 13. The position and the compressing pressure of the compression paddle 18 are controlled by a compression paddle controller 34.

Figure 3:
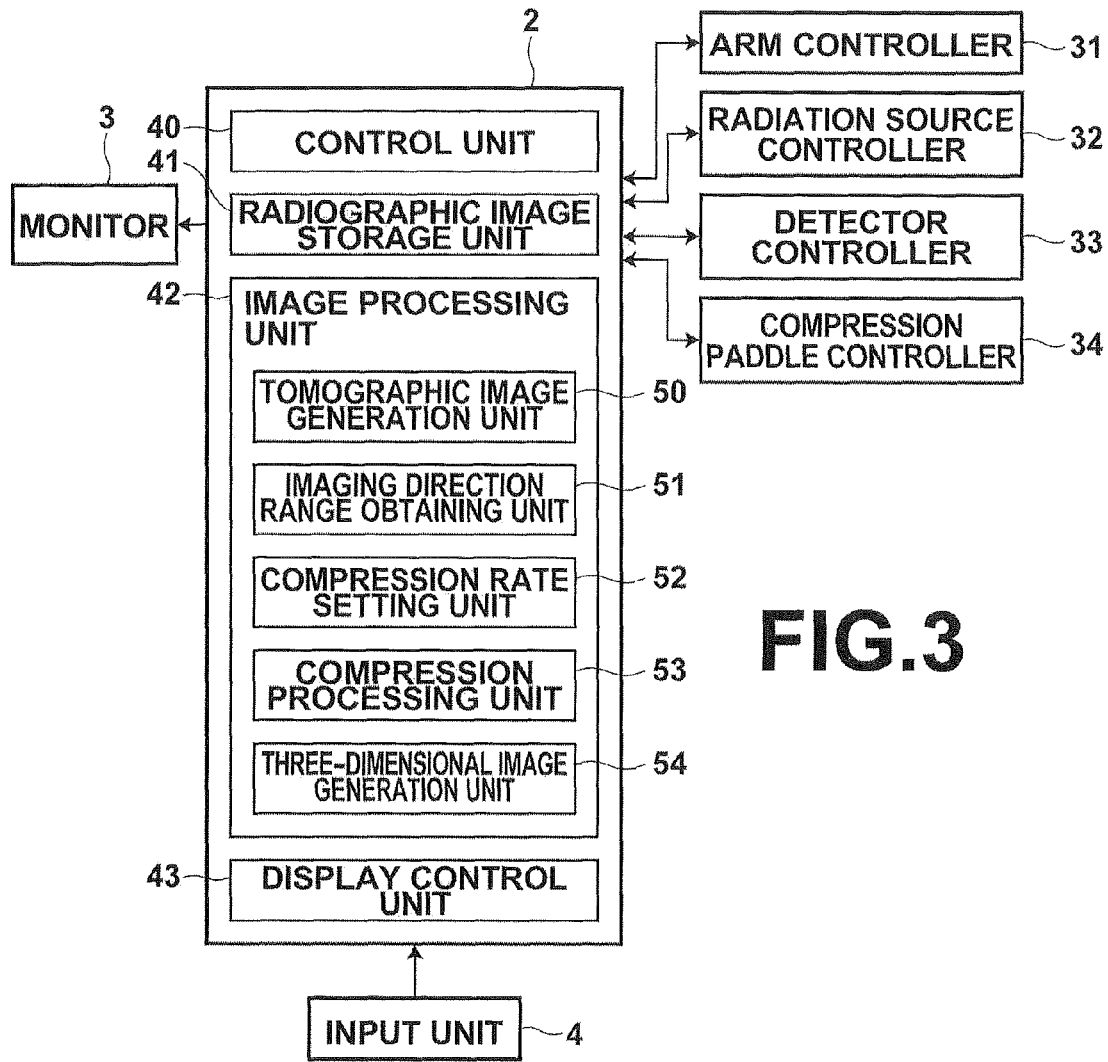
FIG. 3 is a block diagram illustrating the schematic internal structure of a computer of the mammographic imaging and display system shown in FIG. 1.

The computer 2 includes a central processing unit (CPU), a storage device, such as a semiconductor memory, a hard disk, a SSD, etc., and these hardware devices form a control unit 40, a radiographic image storage unit 41, an image processing unit 42 and a display control unit 43, as shown in FIG. 3.

The control unit 40 outputs predetermined control signals to the controllers 31 to 34 to control the entire system. A specific control method will be described in detail later.

The radiographic image storage unit 41 obtains and stores a plurality of radiographic images detected by the radiographic image detector 15 in the imaging operations from different imaging directions. It should be noted that, in this embodiment, the radiographic image storage unit 41 corresponds to a radiographic image obtaining unit recited in the claims.

The image processing unit 42 includes a tomographic image generation unit 50, an imaging direction range obtaining unit 51, a compression rate setting unit 52, a compression processing unit 53 and a three-dimensional image generation unit 54.

The tomographic image generation unit 50 reads out the radiographic images stored in the radiographic image storage unit 41 and generates a tomographic image of a desired slice plane of the breast M using the radiographic images. A method for generating the tomographic image will be described in detail later.

The imaging direction range obtaining unit 51 obtains information of the range of the imaging directions of the radiographic images used to generate one tomographic image at the tomographic image generation unit 50. Specifically, in this embodiment, about ten to twenty radiographic images are obtained with changing the imaging direction in the range of ±25 relative to the direction perpendicular to a breast placement surface of the imaging table 14 (the detection surface of the radiographic image detector 15). The imaging direction range obtaining unit 51 obtains the information of the range of the imaging directions of the radiographic images used to generate the tomographic image among the radiographic images taken in the range of ±25°.

The information of the range of imaging directions is inputted by the user via the input unit 4, such as by inputting "±15°" or "±20", for example, as the information of the range of imaging directions. In a case where "±15°" is inputted as the range of imaging directions, the tomographic image generation unit 50 uses the radiographic images of the imaging directions in the range of ±15° to generate a plurality of tomographic images. In a case where "±20°" is inputted as the range of imaging directions, the tomographic image generation unit 50 uses the radiographic images of the imaging directions in the range of ±20° to generate a plurality of tomographic images.

The information of the range of imaging directions obtained by the imaging direction range obtaining unit 51 is also outputted to the compression rate setting unit 52.

The compression rate setting unit 52 sets a compression rate of compression processing performed by the compression processing unit 53 based on the information of the range of imaging directions inputted thereto.

The compression processing performed by the compression processing unit 53 of this embodiment is processing to compress the tomographic images generated by the tomographic image generation unit 50 with respect to the direction perpendicular to the slice planes thereof. Specifically, in this embodiment, the compression processing is achieved by stacking a predetermined number of tomographic images per unit and adding and averaging (i.e., by calculating an arithmetic mean of) the tomographic images.

Figure 4:
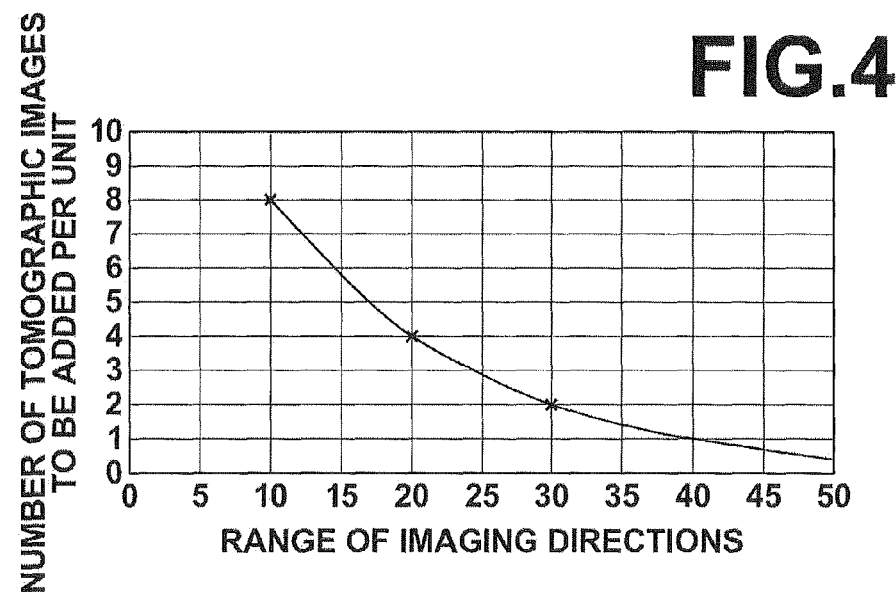
FIG. 4 is a diagram showing a relationship between a range of imaging directions of radiographic images and the number of tomographic images to be added per unit (compression rate)

Therefore, the compression rate setting unit 52 of this embodiment sets, as the compression rate, the number of tomographic images per unit to be added in the compression processing. Specifically, as shown in FIG. 4, a function that associates the range of imaging directions of radiographic images with the number of tomographic images to be added per unit is set in the compression rate setting unit 52. Based on this function and the information of the range of imaging directions inputted thereto, the compression rate setting unit 52 sets the number of tomographic images to be added per unit as the compression rate. It should be noted that the values along the horizontal axis of the graph shown in FIG. 4 are obtained by adding the range of imaging directions in the "+" direction and the range of imaging directions in the "−" direction. Therefore, if the range of imaging directions obtained by the imaging direction range obtaining unit 51 is ±10°, for example, this range corresponds to the range of imaging directions of 20° in the graph shown in FIG. 4, and if the range of imaging directions obtained by the imaging direction range obtaining unit 51 is ±7.5°, this range corresponds to the range of imaging directions of 15° in the graph shown in FIG. 4.

Then, if the inputted range of imaging directions is 20° (±10), for example, the compression rate setting unit 52 obtains "4" as the number of tomographic images to be added per unit (the compression rate). If the inputted range of imaging directions is 10° (±5°), for example, the compression rate setting unit 52 obtains "8" as the number of tomographic images to be added per unit (the compression rate).

As shown in the graph of FIG. 4, the compression rate setting unit 52 of this embodiment sets a smaller number of tomographic images to be added per unit, i.e., a smaller compression rate for a larger range of imaging directions. The reason of setting the compression rate in this manner is as follows.

First, it is said, in general, that, as the inclination of the direction in which the radiation is applied to the subject, i.e., the imaging direction relative to the direction perpendicular to the detection surface of the radiographic image detector 15 (the subject placement surface) is increased, the sharpness and the resolution of the radiographic image are reduced. This is because that a greater inclination of the imaging direction means a greater inclination of the incident angle of radiation passing through a given point in the subject and entering the detection surface of the radiographic image detector 15. Then, an electric charge signal generated by the radiation entering the detection surface at such an inclined direction is detected across a plurality of pixels (a plurality detection elements) rather than at one pixel (one detection element).

Therefore, when the compression processing at a high compression rate is applied to images with low sharpness and resolution, blur, etc., are emphasized, resulting in significantly degraded image quality.

The compression rate setting unit 52 of this embodiment, therefore, sets a smaller compression rate for a larger range of imaging directions.

Based on the compression rate set by the compression rate setting unit 52, the compression processing unit 53 applies the compression processing to the plurality of tomographic images generated by the tomographic image generation unit 50 to generate compressed tomographic images. Specifically, the compression processing unit 53 of this embodiment achieves the compression processing by calculating an arithmetic mean of the predetermined number of tomographic images per unit, as described above. However, the method for achieving the compression processing is not limited to this method, and any other method may be used. Specifically, for example, any one of the predetermined number of tomographic images per unit set by the compression rate setting unit 52 may be selected and the selected tomographic image may be used as the compressed tomographic image. That is, the compression processing may be achieved by performing so-called decimation.

Based on the plurality of compressed tomographic images generated by the compression processing unit 53, the three-dimensional image generation unit 54 generates a three-dimensional image of the breast. Specifically, the three-dimensional image generation unit 54 performs volume rendering using the compressed tomographic images inputted thereto to generate the three-dimensional image.

The display control unit 43 applies predetermined processing to the three-dimensional image generated by the three-dimensional image generation unit 54, the tomographic images generated by the tomographic image generation unit 50 and/or the compressed tomographic images generated by the compression processing unit 53 and displays the images on the monitor 3.

The input unit 4 is formed by a pointing device, such as a keyboard and a mouse, and receives an input of setting of the information of the range of imaging directions, as described above. The input unit 4 also receives an input of settings of imaging conditions, etc., an input of an instruction to start imaging, an input of settings of a display method for displaying the three-dimensional image and/or the tomographic image on the monitor 3, etc.

Next, operation of the mammographic imaging and display system 1 of this embodiment is described with reference to the flow chart shown in FIG. 5.

First, a breast M of the patient is placed on the imaging table 14, and the breast M is compressed by the compression paddle 18 at a predetermined pressure (S10).

Figure 6:
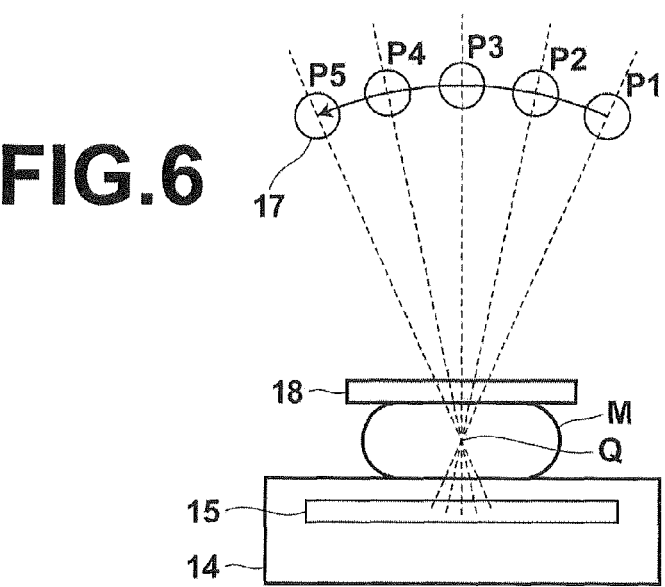
FIG. 6 is a diagram showing changes of the position of a radiation source of the mammographic imaging and display system shown in FIG. 1 from the start of imaging to the end of imaging, and a radiation exposure point Q.

Then, various imaging conditions are inputted by the operator via the input unit 4, and an instruction to start imaging is inputted. When the instruction to start imaging is inputted, the arm controller 31 rotates the arm 13. FIG. 6 shows changes of the position of the radiation source 17 from the start of imaging to the end of imaging, and a radiation exposure point Q.

Specifically, first, the arm controller 31 rotates the arm 13 to bring the radiation source 17 into a position P1. In this embodiment, the position P1 corresponds to the imaging direction of ±25°.

Then, the radiation source controller 32 controls the radiation source 17 so that the radiation is directed to the exposure point Q based on the radiation generation conditions of the radiation emitted from the position P1. It is preferred that the exposure point Q is a point about 2 cm above the center of the breast M placed on the top of the imaging table 14. Then, a radiographic image of the breast M is recorded as a latent charge image on the radiographic image detector 15.

Subsequently, the radiographic image recorded as the latent charge image on the radiographic image detector 15 is read out under control by the detector controller 34. The read out radiographic image is inputted to the computer 2 and stored in the radiographic image storage unit 41.

Then, the radiation source 17 is moved along an arcuate trajectory in the vicinity of the chest wall of the subject under control by the controllers, and a radiographic image of the breast is obtained for each position Pn (n=1 to 5 in the example shown in FIG. 6) along the trajectory and stored in the radiographic image storage unit 41 (S12).

It should be noted that, although only the five positions P1 to P5 are shown in FIG. 6 for the convenience of explanation, about ten to twenty radiographic images in the range of about ±25° relative to the direction perpendicular to the subject placement surface of the imaging table 14 (the detection surface of the radiographic image detector 15) are obtained in actual imaging operations, as mentioned above. The position P5 in this embodiment corresponds to an imaging direction of −25°.

Then, the information of the range of imaging directions of the radiographic images used to generate one tomographic image is inputted by the user via the input unit 4, and the information of the range of imaging directions is obtained by the imaging direction range obtaining unit 51 (S14). Then, the range of imaging directions obtained by the imaging direction range obtaining unit 51 is outputted to the tomographic image generation unit 50 and the compression rate setting unit 52.

Based on the inputted range of imaging directions, the tomographic image generation unit 50 reads out the radiographic images in the range of imaging directions from the radiographic image storage unit 41, and generates tomographic images based on the radiographic images (S16).

Now, a method for generating a tomographic image in a case where the maximum range of ±25° (50°) is inputted as the range of imaging directions, for example, is described.

Figure 7:
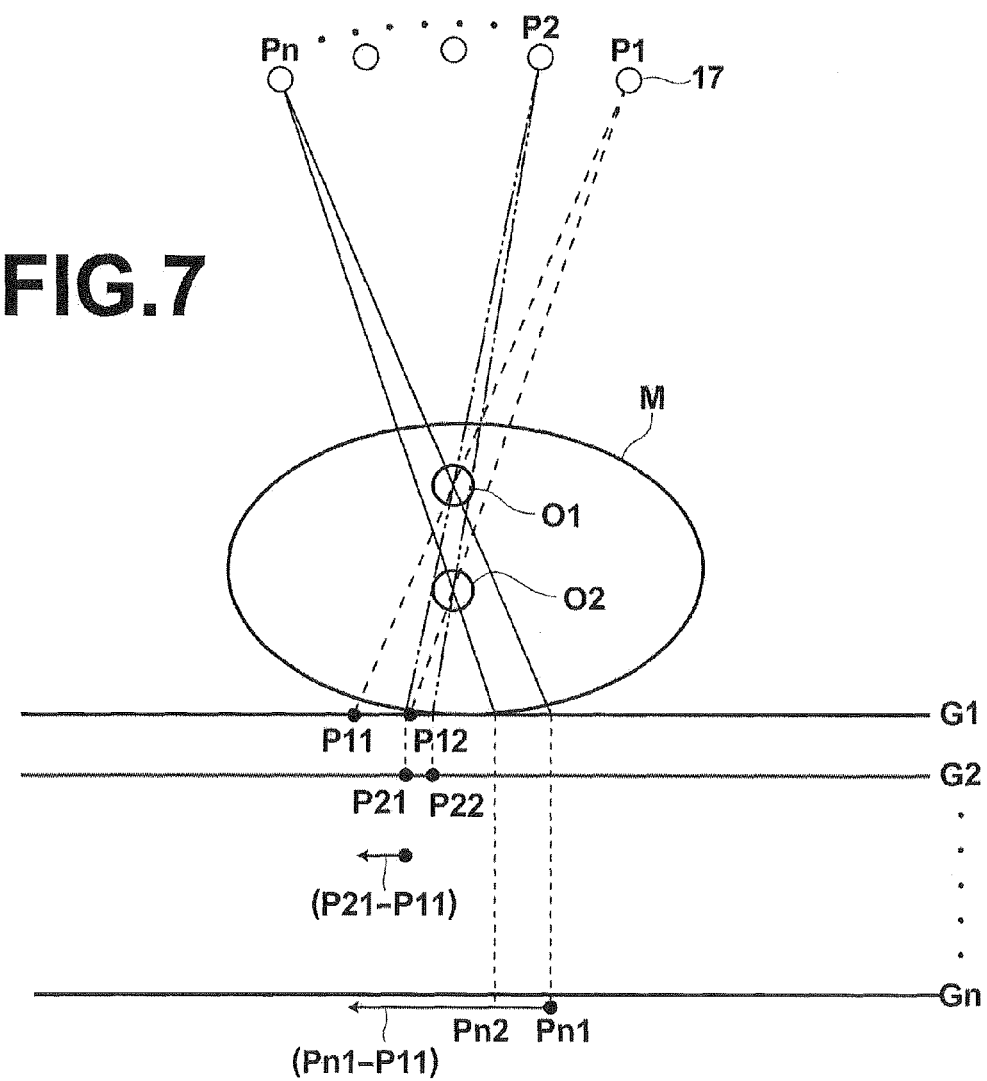
FIG. 7 is a diagram for explaining a method for generating a tomographic image based on a plurality of radiographic images.

First, as shown in FIG. 7, the radiation source 17 is moved to each position P1, P2, . . . , and Pn, and radiation is applied to the breast M from each position to obtain radiographic images G1, G2, . . . , and Gn.

In a case where objects (O1, O2) present at different depths are projected from the position P1, for example, projection images of the objects appear at positions P11 and P12, respectively, on the radiographic image G1. When the objects (O1, O2) are projected from the position P2, projection images of the objects appear at positions P21 and P22, respectively, on the radiographic image G2. By repeating projection from the different radiation source positions P1, P2, . . . , and Pn in this manner, the object O1 is projected at positions P11, P21, . . . , and Pn1 and the object O2 is projected at positions P12, P22, . . . , and Pn2 correspondingly to the different radiation source positions.

Then, if it is wished to emphasize a slice plane where the object O1 is present, the radiographic image G2 is shifted by a distance of (P21-P11), the radiographic image G3 is shifted by a distance of (P31-P11), and the remaining radiographic image are shifted similarly to shift each taken image Gn by a distance of (Pn1-P11), and the thus shifted images are added to generate a tomographic image with a structure in the slice plane at the depth of the object P1 being emphasized.

If it is wished to emphasize a slice plane where the object O2 is present, the radiographic image G2 is shifted by a distance of (P22-P12), the radiographic image G3 is shifted by a distance of (P32-P12), and the remaining radiographic image are shifted similarly to shift each radiographic image Gn by a distance of (Pn2-P12), and the thus shifted images are added. By adding the radiographic images G1, G2, . . . , Gn with aligning the radiographic images depending on the position of the necessary slice in this manner, a tomographic image with a desired slice plane being emphasized can be obtained. It should be noted that, in this embodiment, a plurality of tomographic images with a slice thickness of 1 mm are generated.

On the other hand, the information of the range of imaging directions obtained by the imaging direction range obtaining unit 51 is inputted to the compression rate setting unit 52. Based on the inputted range of imaging directions and the function shown in FIG. 4, the compression rate setting unit 52 calculates and sets the number of tomographic images to be added per unit as the compression rate (S18). Specifically, if the range of imaging directions is 10° (±5°), for example, a compression rate of "8" is set according to the function shown in FIG. 4. It should be noted that, if a value calculated based on the function shown in FIG. 4 is not an integer, the value is rounded to the nearest integer or truncated into an integer.

Then, the compression rate set by the compression rate setting unit 52 is outputted to the compression processing unit 53. Based on the inputted compression rate, the compression processing unit 53 applies the compression processing to the tomographic images generated by the tomographic image generation unit 50 to generate compressed tomographic images (S20).

Specifically, in a case where the compression rate set by the compression rate setting unit 52 is "8", the breast thickness of the breast M is 40 mm and 40 tomographic images are generated, an arithmetic mean is calculated for each unit of eight tomographic images to generate a compressed tomographic image, and therefore five compressed tomographic images are generated. Further, specifically, in a case where the compression rate set by the compression rate setting unit 52 is "4" (the range of imaging directions is 20°), the breast thickness of the breast M is 40 mm and 40 tomographic images are generated, an arithmetic mean is calculated for each unit of four tomographic images to generate a compressed tomographic image, and therefore ten compressed tomographic images are generated.

Then, the compressed tomographic images generated by the compression processing unit 53, as described above, are outputted to the three-dimensional image generation unit 54, and the three-dimensional image generation unit 54 performs volume rendering by using the inputted compressed tomographic images to generate a three-dimensional image of the breast M (S22).

Subsequently, the three-dimensional image generated by the three-dimensional image generation unit 54 is outputted to the display control unit 43. The display control unit 43 applies predetermined processing to the three-dimensional image inputted thereto and displays the three-dimensional image of the breast M on the monitor 3 (S24).

If the user observing the three-dimensional image of the breast M displayed on the monitor 3 wishes to change the compression rate (S26: YES), the user inputs setting of a desired compression rate via the input unit 4 (S18). It should be noted that, in this embodiment, the input unit 4 corresponds to a compression rate change receiving unit recited in the claims.

Then, based on the compression rate set and inputted, the generation of compressed tomographic images and the generation of a three-dimensional image are performed again, and the generated three-dimensional image is displayed on the monitor 3 (S20 to S24). The user can repeatedly change the compression rate until a satisfactory three-dimensional image is displayed. When a three-dimensional image satisfactory to the user is displayed, the process ends.

According to the above-described mammographic imaging and display system 1 of the first embodiment, a plurality of tomographic images of the breast M are generated based on a plurality of radiographic images, and the generated tomographic images are subjected to compression processing in the direction perpendicular to the slice planes of the tomographic images to generate compressed tomographic images. Then, by reconstructing a three-dimensional image using the compressed tomographic images, the dimension size in the Z-direction (the direction perpendicular to the slice planes) can be made close to the dimension sizes in the X-direction and Y-direction. This allows making the size of a structure in the three-dimensional image close to the actual size of the structure, thereby facilitating understanding of the three-dimensional structure and improving the diagnosis accuracy.

Further, by obtaining the range of imaging directions of the radiographic images used to generate the tomographic images and setting the compression rate of the compression processing based on the obtained range of imaging directions, the compression processing can be performed without degrading the image quality of the compressed tomographic images.

Figure 8:
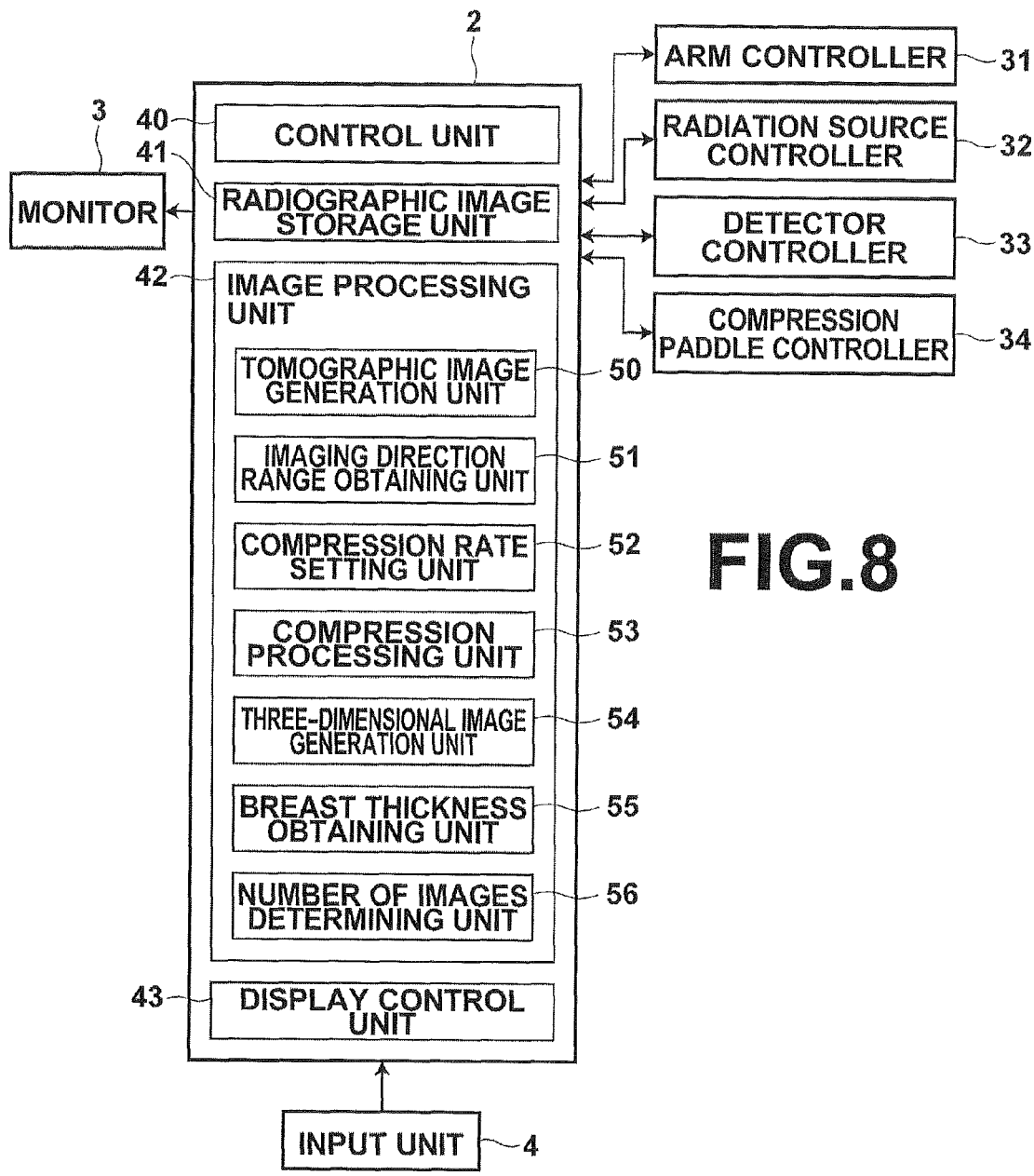
FIG. 8 is a diagram illustrating the schematic structure of a mammographic imaging and display system employing a second embodiment of the tomographic image generation device of the invention.

Next, a mammographic imaging and display system employing a second embodiment of the tomographic image generation device and method of the invention is described. FIG. 8 illustrates the internal configuration of the computer 2 of the mammographic imaging and display system of the second embodiment. The mammographic imaging and display system of the second embodiment includes a breast thickness obtaining unit 55 and a number of images determining unit 56 in addition to the components of the mammographic imaging and display system 1 of the first embodiment. The mammographic imaging and display system of the second embodiment is configured to limit the number of compressed tomographic images to be generated by setting the compression rate so that a burden imposed on the user observing the compressed tomographic images is reduced.

The breast thickness obtaining unit 55 obtains the thickness of the breast M compressed by the compression paddle 18. Specifically, the compression paddle controller 34 detects positional information of the compression paddle 18 compressing the breast M, and calculates, based on the positional information, a distance between the breast placement surface and the compression paddle 18 as the breast thickness. Then, the breast thickness obtaining unit 55 obtains the breast thickness calculated by the compression paddle controller 34, as described above.

The number of images determining unit 56 calculates the total number of compressed tomographic images to be generated by the compression processing based on the breast thickness obtained by the breast thickness obtaining unit 55 and the compression rate set by the compression rate setting unit 52, and determines whether or not the total number of compressed tomographic images is not greater than a threshold value that is set in advance.

Next, operation of the mammographic imaging and display system of the second embodiment is described with reference to the flow chart shown in FIG. 9.

Figure 5:
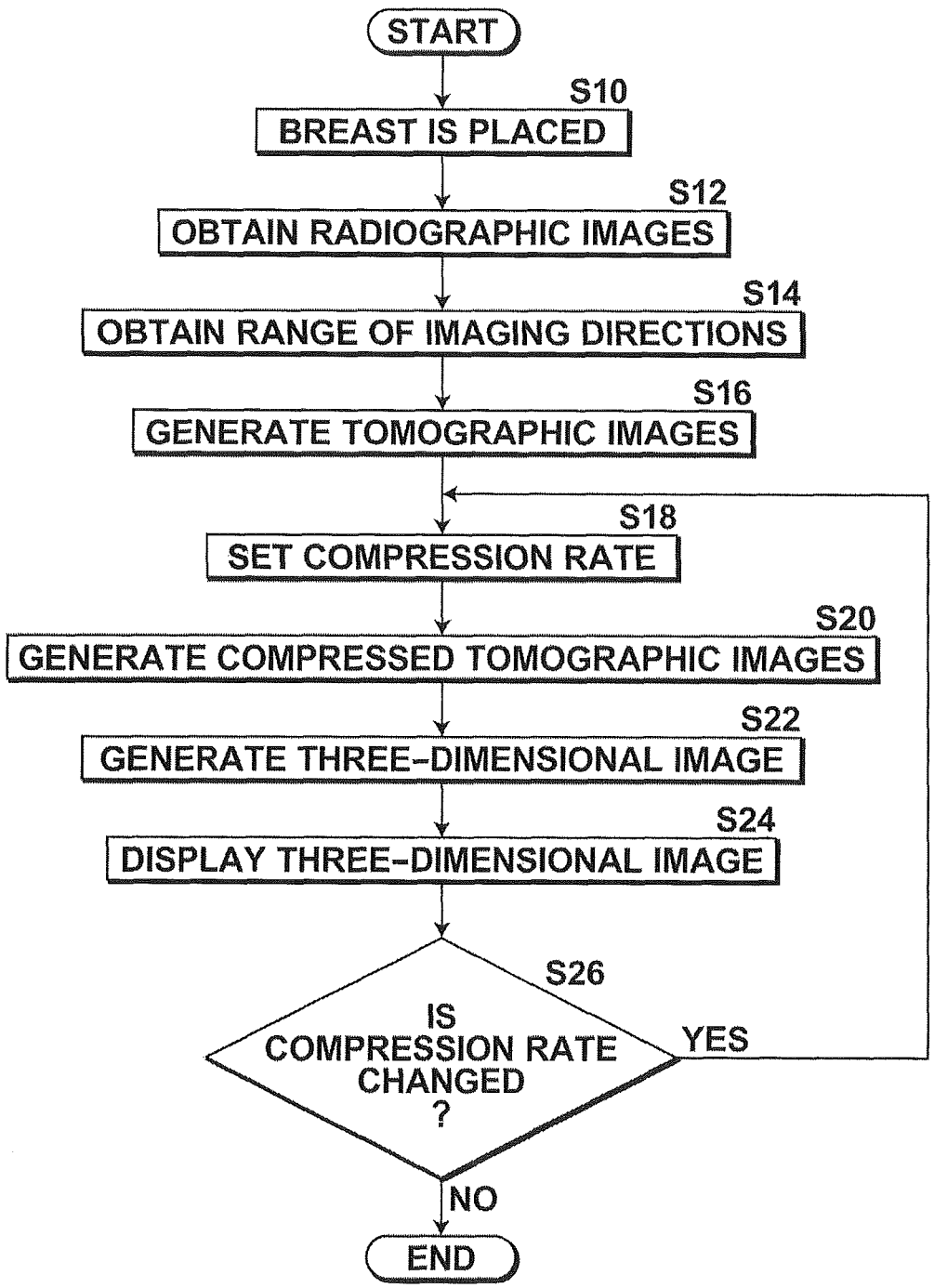
FIG. 5 is a flow chart for explaining operation of a mammographic imaging and display system employing a first embodiment of the tomographic image generation device of the invention.
Figure 9:
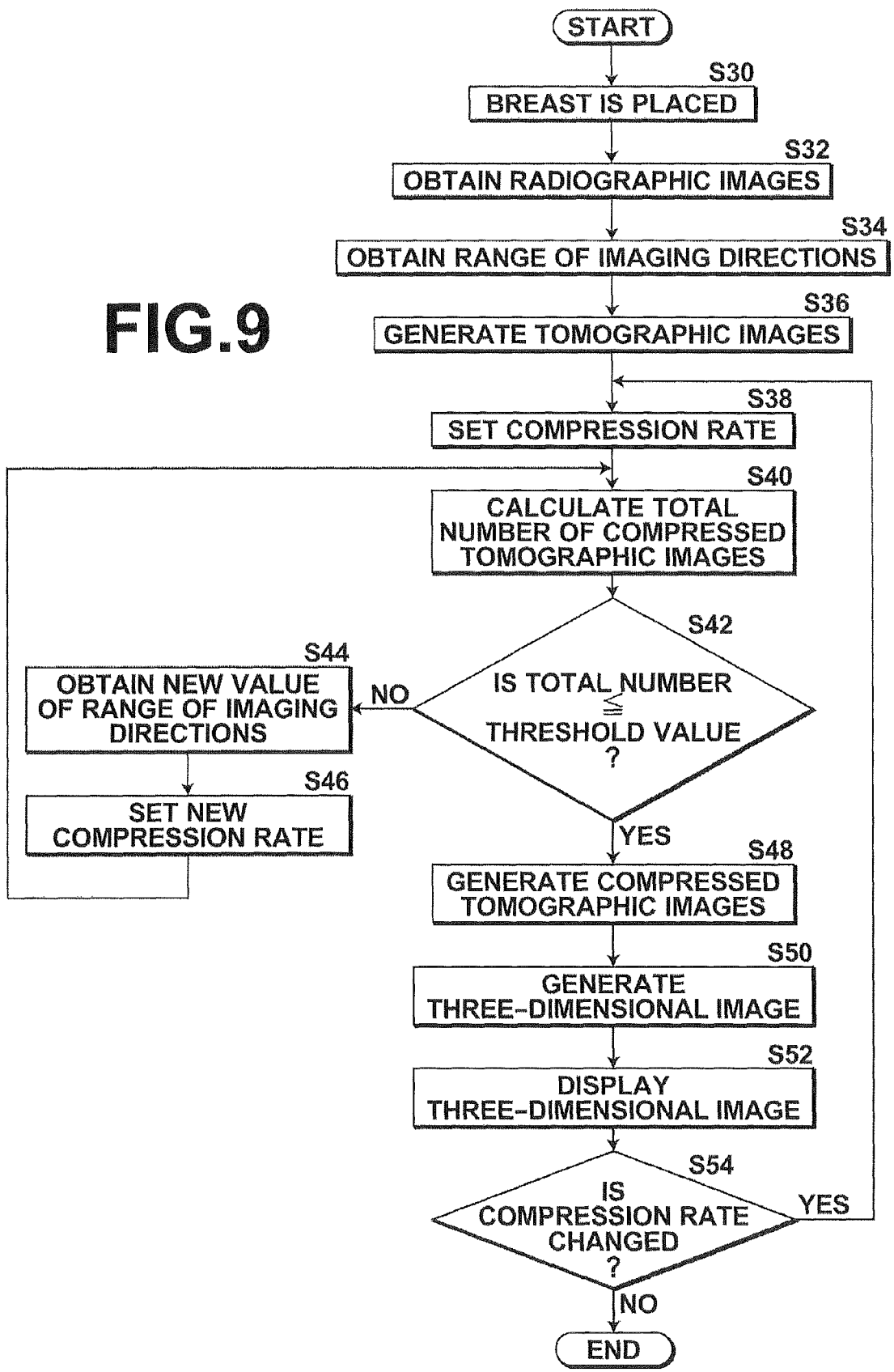
FIG. 9 is a flow chart for explaining operation of the mammographic imaging and display system employing the second embodiment of the tomographic image generation device of the invention.

Operations from the placement of the breast (S30) to the setting of the compression rate (S38) shown in FIG. 9 are the same as those of the mammographic imaging and display system 1 of the first embodiment (S10 to S18 shown in FIG. 5).

Then, in the mammographic imaging and display system of the second embodiment, after the compression rate is set by the compression rate setting unit 52, the total number of the compressed tomographic images to be generated by the compression processing is calculated based on the compression rate and the breast thickness obtained by the breast thickness obtaining unit 55 (S40).

Specifically, in a case where the breast thickness obtained by the breast thickness obtaining unit 55 is 80 mm, for example, the value of 80 mm of the breast thickness is outputted to the number of images determining unit 56.

The number of images determining unit 56 first calculates the number of tomographic images to be generated based on the breast thickness of 80 mm and the slice thickness of 1 mm of each tomographic image, namely, 80 mm/1 mm=80.

Then, based on the number of tomographic images and the compression rate set by the compression rate setting unit 52, the number of images determining unit 56 calculates the total number of compressed tomographic images to be generated by the compression processing (S40). Specifically, in a case where the compression rate is "8" (the range of imaging directions is 10°), for example, the number of images determining unit 56 calculates 80/8=10 as the total number of compressed tomographic images. In a case where the compression rate is "4" (the range of imaging directions is 20°), for example, the number of images determining unit 56 calculates 80/4=20 as the total number of compressed tomographic images.

Then, the number of images determining unit 56 compares the thus calculated total number of compressed tomographic images with the threshold value set in advance (which is assumed to be 15 in this embodiment), and determines whether or not the total number of compressed tomographic images is not greater than the threshold value of 15 (S42). It should be noted that, although the threshold value of 15 is set in advance in this embodiment, this is not intended to limit the invention, and any other threshold value may be set in view of reducing the burden of observation of the compressed tomographic images.

If it is determined by the number of images determining unit 56 that the total number of compressed tomographic images is not greater than the threshold value (S42: YES), information to that effect is outputted to the compression processing unit 53. Then, the compression processing unit 53 applies the compression processing to the tomographic images based on the compression rate set by the compression rate setting unit 52 and generates the compressed tomographic images (S48). The following operations from the generation of a three-dimensional image (S50) to the changing of the compression rate (S54) are the same as those of the mammographic imaging and display system 1 of the first embodiment (S22 to S26 shown in FIG. 5).

In contrast, if it is determined by the number of images determining unit 56 that the total number of compressed tomographic images is greater than the threshold value (S42: NO), information to that effect is outputted to the display control unit 43, and the display control unit 43 displays, on the monitor 3, a message, or the like, for prompting the user to enter a new value of the range of imaging directions.

The user observing the message, or the like, displayed on the monitor 3 enters a new value of the range of imaging directions via the input unit 4, and the inputted value of the range of imaging directions is obtained by the imaging direction range obtaining unit 51 (S44). The value of the range of imaging directions entered by the user at this time is smaller than the previously inputted value of the range of imaging directions. The decrement of the value of the range of imaging directions to be entered may be 1°, or the value may be selected by the user from choices at 5° intervals, such as 10°, 15° and 20°, for example.

Then, the range of imaging directions obtained by the imaging direction range obtaining unit 51 is outputted to the compression rate setting unit 52, and the compression rate setting unit 52 sets a new compression rate based on the new value of the range of imaging directions inputted thereto (S46).

The new compression rate set by the compression rate setting unit 52 is inputted to the number of images determining unit 56, and the number of images determining unit 56 calculates the total number of compressed tomographic images based on the new compression rate inputted thereto (S40). Then, the number of images determining unit 56 compares the total number of compressed tomographic images with the threshold value of 15 set in advance, and determines whether or not the total number of compressed tomographic images is not greater than the threshold value of 15 (S42).

The operations to obtain a new value of the range of imaging directions, to set a new compression rate and to compare the total number of compressed tomographic images with the threshold value are repeated until the number of images determining unit 56 determines that the total number of compressed tomographic images is not greater than the threshold value.

The operations performed after it is determined by the number of images determining unit 56 that the total number of compressed tomographic images is not greater than the threshold value are as described above.

In the mammographic imaging and display system of the second embodiment, not only the three-dimensional image generated by the three-dimensional image generation unit 54 but also the compressed tomographic images generated by the compression processing unit 53 are displayed on the monitor 3. The compressed tomographic images may be displayed in the form of a list or may be displayed one by one with changing the displayed compressed tomographic image when an instruction to change the displayed compressed tomographic image is received via the input unit 4.

According to the above-described mammographic imaging and display system of the second embodiment, the total number of compressed tomographic images to be generated by the compression processing is obtained based on the compression rate that is set depending on the range of imaging directions, and whether or not the total number is not greater than the threshold value is determined. If it is determined that the total number of compressed tomographic images is greater than the threshold value, a new value of the range of imaging directions is obtained, and a new compression rate of the compression processing is set based on the obtained new value of the range of imaging directions. This allows limiting the total number of the compressed tomographic images, thereby reducing the time taken for image interpretation of the compressed tomographic images.

Although the cases where the three-dimensional image and/or the compressed tomographic images are displayed on the monitor 3 are described in the description of the mammographic imaging and display systems of the first and second embodiments, this is not intended to limit the invention. For example, the tomographic images before being compressed or the radiographic images before generation of the tomographic images may be displayed on the monitor 3.

Figure 10:
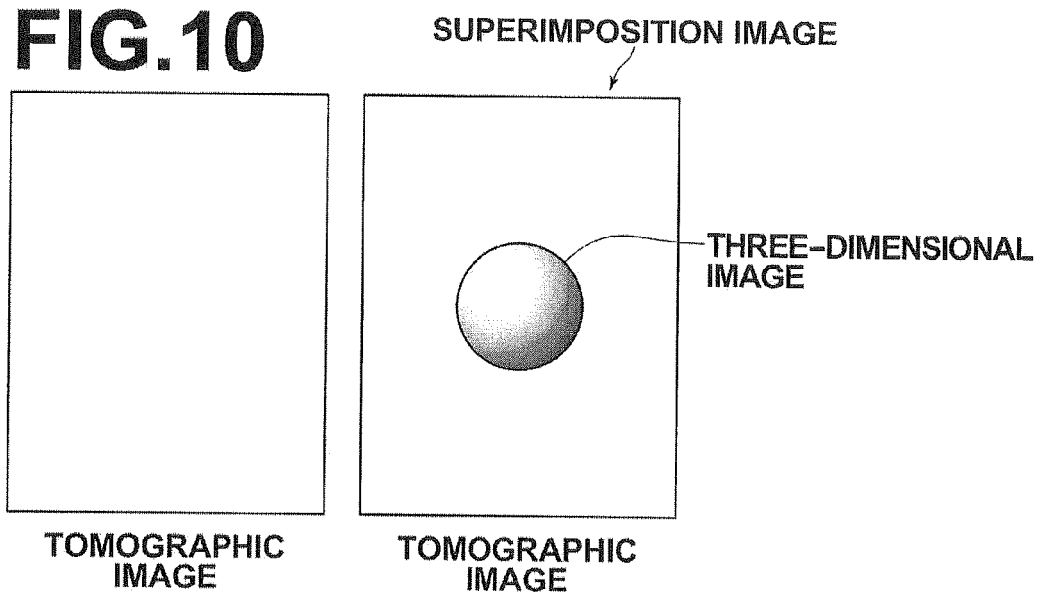
FIG. 10 is a diagram showing one example of a display where a tomographic image and a superimposition image of a three-dimensional image superimposed on the tomographic image are shown side by side.

Further, as shown in FIG. 10, for example, a desired one of the tomographic images generated by the tomographic image generation unit 50 may be displayed side by side with a superimposition image of a three-dimensional image of an area specified by the user on the tomographic image via the input unit 4 superimposed on the tomographic image. It should be noted that, in this embodiment, the input unit 4 corresponds to an area specifying unit recited in the claims.

Although the case where a tomographic image is displayed side by side with a superimposition image of a three-dimensional image superimposed on the tomographic image on the monitor 3 is shown in FIG. 10 as an example, this is not intended to limit the invention. For example, a compressed tomographic image or a radiographic image may be displayed side by side with a superimposition image of a three-dimensional image superimposed on the compressed tomographic image or radiographic image on the monitor 3.

Figure 11:
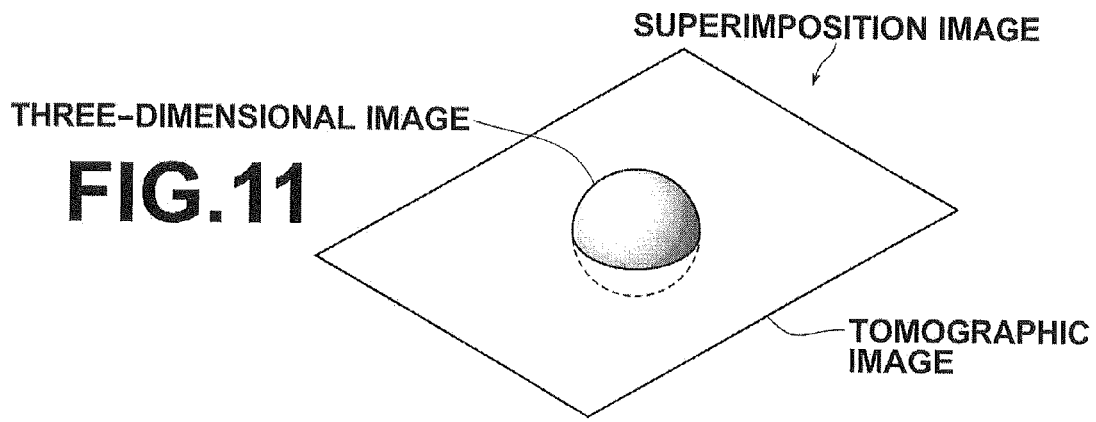
FIG. 11 is a diagram showing one example of a display of the superimposition image in a rotated state.

The above-described superimposition image may be displayed to be rotatable according to an input by the user via the input unit 4. FIG. 11 shows a state where a superimposition image of a three-dimensional image superimposed on a tomographic image is rotated in a given direction by a given angle from the state shown in FIG. 10.

Figure 12:
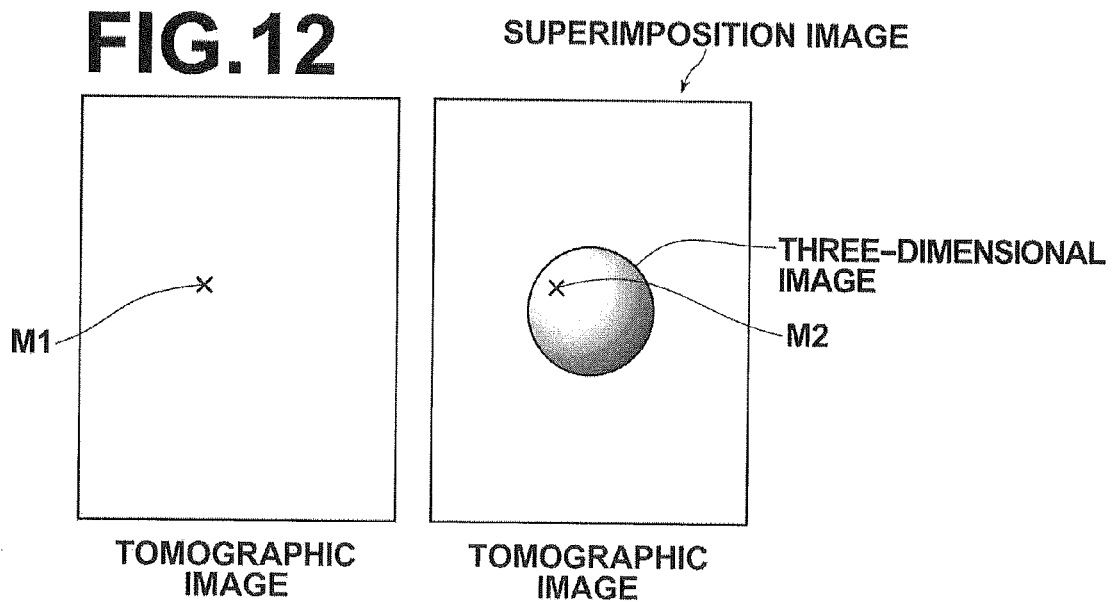
FIG. 12 is a diagram showing one example of a display where markers are displayed at corresponding positions on the tomographic image and on the superimposition image.

Further, in the case where a tomographic image, a compressed tomographic image or a radiographic image is displayed side by side with a superimposition image of a three-dimensional image superimposed on the tomographic image, compressed tomographic image or radiographic image on the monitor 3, a marker M1 may be displayed at a position on the subject in the tomographic image, compressed tomographic image or radiographic image and a marker M2 may be displayed at a corresponding position on the subject in the superimposition image, as shown in FIG. 12, in order to facilitate recognition of corresponding positions on the two images. In this case, for example, when an input to specify the position of the marker M1 on the tomographic image, compressed tomographic image or radiographic image is received, the marker M2 may be displayed at the position corresponding to the position of the marker M1. Alternatively, when an input to specify the position of the marker M2 on the superimposition image is received, the marker M1 may be displayed at the position on the tomographic image, compressed tomographic image or radiographic image corresponding to the position of the marker M2.

Further, the tomographic image, compressed tomographic image or radiographic image on which the three-dimensional image is superimposed may be arbitrarily selected by the user via the input unit 4. At this time, a screen for selecting the image to be displayed, such as a screen displaying the tomographic images, the compressed tomographic image or the radiographic images in a list, may be displayed on the monitor 3. It should be noted that, in this embodiment, the input unit 4 corresponds to an image selection receiving unit recited in the claims.

The shape of the three-dimensional image superimposed on the tomographic image, compressed tomographic image or radiographic image may be spherical, as shown in FIGS. 10 to 11, or may be cuboidal or ellipsoidal.

The position and/or the display range of the three-dimensional image superimposed on the tomographic image, compressed tomographic image or radiographic image may be arbitrarily set by the user via the input unit 4. Specifically, for example, the user may specify the position and the range of an area on the tomographic image, compressed tomographic image or radiographic image where a tumor may possibly be present or which is difficult to observe due to dense mammary gland as judged by the user, and a three-dimensional image of the specified range with the specified position being the center or centroid thereof may be superimposed on the tomographic image, compressed tomographic image or radiographic image and displayed.

The shape of the range of the three-dimensional image specified by the user may be spherical or cuboidal, for example, or, if the user specifies the range of a three-dimensional image with respect to the mammary gland, for example, an inclined elongated range may be specified. When such an elongated range is specified, the user may specify the start point and the end point of the range. It should be noted that, in this embodiment, the input unit 4 corresponds to a display range receiving unit recited in the claims.

The color of the three-dimensional image superimposed on the tomographic image, compressed tomographic image or radiographic image may be arbitrarily set by the user via the input unit 4. At this time, a color template for setting the color of the three-dimensional image may be displayed on the monitor 3. It should be noted that, in this embodiment, the input unit 4 corresponds to a color change receiving unit recited in the claims.

When the above-described superimposition image is displayed, it is desirable to display the tomographic image, compressed tomographic image or radiographic image and the three-dimensional image in different colors. For example, the tomographic image, compressed tomographic image or radiographic image may be displayed in black-and-white and the three-dimensional image may be displayed in color.

Although the tomographic image generation device and method of the invention are applied to the mammographic imaging and display system in the above-described embodiments, the subject in the invention is not limited to the breast. For example, the invention is also applicable to a radiographic imaging and display system provided with a tomosynthesis imaging function for so-called "general radiography" for imaging the chest, the head, or the like. In the case where the invention is applied to a radiographic imaging and display system for general radiography, information of the thickness of the subject may be obtained using an optical sensor, for example, or may be manually set and inputted by the user.

What is claimed is:

1. A tomographic image generation device comprising:
    a radiographic image obtaining unit for obtaining radiographic images for different imaging directions taken by applying radiation to a subject from the different imaging directions;
    a tomographic image generation unit for generating a plurality of tomographic images of the subject based on the plurality of radiographic images obtained by the radiographic image obtaining unit;
    a compression processing unit for applying compression processing in a direction perpendicular to slice planes of the tomographic images to the tomographic images generated by the tomographic image generation unit to generate compressed tomographic images;
    an imaging direction range obtaining unit for obtaining a range of the imaging directions; and
    a compression rate setting unit for setting a compression rate of the compression processing based on the range of imaging directions obtained by the imaging direction range obtaining unit.

2. The tomographic image generation device as claimed in claim 1, further comprising a number of images determining unit for obtaining a total number of the compressed tomographic images to be generated based on the compression rate set by the compression rate setting unit and determining whether or not the total number is not greater than a threshold value,
    wherein, if it is determined by the number of images determining unit that the total number of the compressed tomographic images is greater than the threshold value, the imaging direction range obtaining unit obtain a new value of the range of imaging directions, and
    the compression rate setting unit set a new compression rate of the compression processing based on the obtained new value of the range of imaging directions.

3. The tomographic image generation device as claimed in claim 1, further comprising a compression rate change receiving unit for receiving a change to the compression rate,
    wherein the compression rate setting unit sets a new compression rate of the compression processing based on a changed compression rate received by the compression rate change receiving unit.

4. The tomographic image generation device as claimed in claim 1, further comprising a three-dimensional image generation unit for generating a three-dimensional image of the subject based on the compressed tomographic images generated by the compression processing unit.

5. The tomographic image generation device as claimed in claim 4, further comprising a display control unit for displaying a superimposition image of the three-dimensional image superimposed on the radiographic image, the tomographic image or the compressed tomographic image.

6. The tomographic image generation device as claimed in claim 5, further comprising an area specifying unit for receiving a specification of a desired area on the radiographic image, the tomographic image or the compressed tomographic image,
    wherein the display control unit displays a superimposition image of the three-dimensional image superimposed on the radiographic image, the tomographic image or the compressed tomographic image, the three-dimensional image containing the area received by the area specifying unit.

7. The tomographic image generation device as claimed in claim 5, wherein the display control unit displays the three-dimensional image and the radiographic image, the tomographic image or the compressed tomographic image of the superimposition image in different colors from each other.

8. The tomographic image generation device as claimed in claim 5, wherein the display control unit displays the radiographic image, the tomographic image or the compressed tomographic image side by side with the superimposition image.

9. The tomographic image generation device as claimed in claim 5, wherein the display control unit displays the superimposition image in a rotated state.

10. The tomographic image generation device as claimed in claim 5, wherein the display control unit displays markers at a position on the subject on the radiographic image, the tomographic image or the compressed tomographic image and a position on the superimposition image corresponding to the position on the subject.

11. The tomographic image generation device as claimed in claim 5, further comprising an image selection receiving unit for receiving a selection of any one of the radiographic images, the tomographic images or the compressed tomographic images to be displayed.

12. The tomographic image generation device as claimed in claim 5, further comprising a color change receiving unit for receiving a change to the color of the three-dimensional image.

13. The tomographic image generation device as claimed in claim 5, further comprising a display range receiving unit for receiving a display range or position of the three-dimensional image.

14. A tomographic image generation method comprising:
obtaining radiographic images for different imaging directions taken by applying radiation to a subject from the different imaging directions;
generating a plurality of tomographic images of the subject based on the obtained plurality of radiographic images; and
applying compression processing in a direction perpendicular to slice planes of the generated tomographic images to the tomographic images to generate compressed tomographic images, wherein a range of the imaging directions is obtained, and a compression rate of the compression processing is set based on the obtained range of the imaging directions.

* * * * *